United States Patent
Tanner et al.

(10) Patent No.: US 9,000,137 B2
(45) Date of Patent: Apr. 7, 2015

(54) NUCLEIC ACID APTAMERS AGAINST PLASMODIUM LACTATE DEHYDROGENASE AND HISTIDINE-RICH PROTEIN II AND USES THEREOF FOR MALARIA DIAGNOSIS

(71) Applicant: The University of Hong Kong, Hong Kong (CN)

(72) Inventors: Julian A Tanner, Hong Kong (CN); Yee Wai Cheung, Hong Kong (CN); Masayo Kotaka, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 13/763,051

(22) Filed: Feb. 8, 2013

(65) Prior Publication Data

US 2013/0210023 A1    Aug. 15, 2013

Related U.S. Application Data

(60) Provisional application No. 61/596,774, filed on Feb. 9, 2012.

(51) Int. Cl.
*C07H 21/04* (2006.01)
*C12Q 1/68* (2006.01)
*G01N 33/53* (2006.01)
*G01N 33/569* (2006.01)

(52) U.S. Cl.
CPC .......... *C12Q 1/6893* (2013.01); *G01N 33/5308* (2013.01); *G01N 33/56905* (2013.01); *G01N 2333/445* (2013.01)

(58) Field of Classification Search
USPC .......................................... 536/23.1; 435/6.15
See application file for complete search history.

(56) References Cited

U.S. PATENT DOCUMENTS

2012/0316325 A1*   12/2012   Ban et al. ..................... 536/23.1

* cited by examiner

*Primary Examiner* — Jon E Angell
(74) *Attorney, Agent, or Firm* — Saliwanchik, Lloyd & Eisenschenk

(57) ABSTRACT

The present invention provides nucleic acid aptamers that bind to *Plasmodium* proteins lactate dehydrogenase and histidine-rich protein II, and uses thereof for the diagnosis of malaria. Aptamers against histidine-rich protein II may be used to detect the presence of *Plasmodium* species in general, whereas aptamers against lactate dehydrogenase can be used to specifically detect *Plasmodium falciparum*.

12 Claims, 15 Drawing Sheets

| Aptamer Target | Aptamer Name | Sequence (5' to 3') | Length (bases) | K$_D$ by ITC (nM) |
|---|---|---|---|---|
| LDH | 2004s SEQ ID NO:1 | ACTCGAGCAGGTGGTAGAATCATAAT GGCCTGATC | 35 | 26 |
| LDH | 2008s SEQ ID NO:2 | CTGGGCGGTAGAACCATAGTGACCCA GCCGTCTAC | 35 | 43 |
| LDH | 2009s SEQ ID NO:3 | TAGGTGGCCAGAAGGTAGAACCATAG TGGTCTGGTA | 36 | 42 |
| LDH | 2021s SEQ ID NO:4 | AGAATGGCGGGAGAGCCTTAGCGAC CATTCGTAC | 34 | 29 |
| HRP2 | 2101s SEQ ID NO:5 | AGCGCATTCATGCGCTCCCGCTTATGC GGGGCGGCCACGTGGAAACCCGGTT TCGCTTGTTCTGCTAGCC | 70 | 85 |
| HRP2 | 2105s SEQ ID NO:6 | TGCCCACTTATGTTCGCCCCCCCCCTC TTGTTCTC | 35 | ND* |
| HRP2 | 2106s SEQ ID NO:7 | GCTTATCCGATGCAGACCCCTTCGGT CCTGCCCTC | 35 | ND* |
| HRP2 | 2112s SEQ ID NO:8 | TGGTCATGCCGTTGGGAGTATCATTCC CCGTACTC | 35 | ND* |
| HRP2 | 2115s SEQ ID NO:9 | CACTCCACTGAGAACTTGCGAGTGGT CCCATTTACCTAGCCGTCCCGCACTG CTGCTTTCTGTGCGGACCGTATC | 76 | 35 |
| HRP2 | 2126s SEQ ID NO:10 | CTGGGGGGTTCTAGGGGGGGGGCA CTTATCTGCA | 35 | 48 |
| HRP2 | 2144s SEQ ID NO:11 | TTATTGGGGGGGTTAGGGGGGGGCTT TTATTCACT | 35 | ND* |

*K$_D$ could not be determined by ITC for these aptamers.

FIG. 3

SEQ ID NO:2
5'-ctgggcggtagaaccatagtgacccagccgtctac-3'

SEQUENCE LISTING

```
<160> NUMBER OF SEQ ID NOS: 20

<210> SEQ ID NO 1
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 1
acgcgagcag gtggtagaat cataatggcc tgatc                                35

<210> SEQ ID NO 2
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 2
ctgggcggta gaaccatagt gacccagccg tctac                                35

<210> SEQ ID NO 3
<211> LENGTH: 36
<212> TYPE: DNA
<213> ORGANISM: Artificial Sequence
<220> FEATURE:
<223> OTHER INFORMATION: the sequence is synthesized

<400> SEQUENCE: 3
taggtggcca gaaggtagaa ccatagtggt ctggta                               36

<210> SEQ ID NO 4
<211> LENGTH: 34
<212> TYPE: DNA
<213> ORGANISM: Artificial Sequence
<220> FEATURE:
<223> OTHER INFORMATION: the sequence is synthesized

<400> SEQUENCE: 4
agaatggcgg gagagcctta gcgaccattc gtac                                 34

<210> SEQ ID NO 5
<211> LENGTH: 70
<212> TYPE: DNA
<213> ORGANISM: Artificial Sequence
<220> FEATURE:
<223> OTHER INFORMATION: the sequence is synthesized

<400> SEQUENCE: 5
agcgcattca tgcgctcccg cttatgcggg gcggccacgt ggaaacccgg tttcgcttgt      60
```
tctgctagcc 70

<210> SEQ ID NO 6
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 6
tgcccactta tgttcgcccc cccctcttg ttctc 35

<210> SEQ ID NO 7
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 7
gcttatccga tgcagacccc ttcggtcctg ccctc 35

<210> SEQ ID NO 8
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 8
tggtcatgcc gttgggagta tcattccccg tacgc 35

<210> SEQ ID NO 9
<211> LENGTH: 76
<212> TYPE: DNA
<213> ORGANISM: Artificial Sequence
<220> FEATURE:
<223> OTHER INFORMATION: the sequence is synthesized

<400> SEQUENCE: 9
cactccactg agaacttgcg agtggtccca ttttacctag ccgtcccgca ctgctgcttt 60
ctgtgcggac cgtatc 76

<210> SEQ ID NO 10
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 10
ctgggggggt tctagggggg gggcacttat ctgca 35

<210> SEQ ID NO 11
<211> LENGTH: 35
<212> TYPE: DNA
<213> ORGANISM: Artificial Sequence
<220> FEATURE:
<223> OTHER INFORMATION: the sequence is synthesized

<400> SEQUENCE: 11 ttattgggggg ggttaggggg gggcttttat tcact 35

<210> SEQ ID NO 12

<211> LENGTH: 43
<212> TYPE: DNA
<213> ORGANISM: Artificial Sequence
<220> FEATURE:
<223> OTHER INFORMATION: the sequence is synthesized

<400> SEQUENCE: 12
attattgcta gcatggcacc aaaagcaaaa atcgttttag ttg    43

<210> SEQ ID NO 13
<211> LENGTH: 43
<212> TYPE: DNA
<213> ORGANISM: Artificial Sequence
<220> FEATURE:
<223> OTHER INFORMATION: the sequence is synthesized

<400> SEQUENCE: 13
attattctcg agttaagcta atgccttcat tctcttagtt tca    43

<210> SEQ ID NO 14
<211> LENGTH: 37
<212> TYPE: DNA
<213> ORGANISM: Artificial Sequence
<220> FEATURE:
<223> OTHER INFORMATION: the sequence is synthesized
<220> FEATURE:
<221> NAME/KEY: misc_feature
<222> LOCATION: (19)..(19)
<223> OTHER INFORMATION: n is a, c, g, or t

<400> SEQUENCE: 14
cgtacggtcg acgctagcnc acgtggagct cggatcc    37

<210> SEQ ID NO 15
<211> LENGTH: 18
<212> TYPE: DNA
<213> ORGANISM: Artificial Sequence
<220> FEATURE:
<223> OTHER INFORMATION: the sequence is synthesized

<400> SEQUENCE: 15
cgtacggtcg acgctagc    18

<210> SEQ ID NO 16
<211> LENGTH: 18
<212> TYPE: DNA
<213> ORGANISM: Artificial Sequence
<220> FEATURE:
<223> OTHER INFORMATION: the sequence is synthesized

<400> SEQUENCE: 16
ggatccgagc tccacgtg    18

<210> SEQ ID NO 17
<211> LENGTH: 37
<212> TYPE: DNA
<213> ORGANISM: Artificial Sequence
<220> FEATURE:
<223> OTHER INFORMATION: the sequence is synthesized

<400> SEQUENCE: 17
attattgaat tcatggcaac tctaaaggat cagctga    37

<210> SEQ ID NO 18
<211> LENGTH: 37
<212> TYPE: DNA
<213> ORGANISM: Artificial Sequence

```
<220> FEATURE:
<223> OTHER INFORMATION: the sequence is synthesized

<400> SEQUENCE: 18
attattaagc ttttaaaatt gcagctcctt ttggatc                              37

<210> SEQ ID NO 19
<211> LENGTH: 44
<212> TYPE: DNA
<213> ORGANISM: Artificial Sequence
<220> FEATURE:
<223> OTHER INFORMATION: the sequence is synthesized

<400> SEQUENCE: 19
attattgcta gcatggcaac tcttaaggaa aaactcattg cacc                      44

<210> SEQ ID NO 20
<211> LENGTH: 39
<212> TYPE: DNA
<213> ORGANISM: Artificial Sequence
<220> FEATURE:
<223> OTHER INFORMATION: the sequence is synthesized

<400> SEQUENCE: 20
attattgcgg ccgctcacag gtcttttagg tccttctgg                            39
```

NUCLEIC ACID APTAMERS AGAINST PLASMODIUM LACTATE DEHYDROGENASE AND HISTIDINE-RICH PROTEIN II AND USES THEREOF FOR MALARIA DIAGNOSIS

CROSS-REFERENCE TO RELATED APPLICATION

This application claims the benefit of U.S. provisional application Ser. No. 61/596,774, filed Feb. 9, 2012, which is herein incorporated by reference in its entirety.

FIELD OF THE INVENTION

The present invention relates to DNA aptamers that specifically bind to *Plasmodium* lactate dehydrogenase (LDH) and histidine-rich protein II (HRPII), and uses thereof for diagnosis of malaria.

BACKGROUND

Malaria, an infectious disease widespread in tropical and subtropical regions, is caused by infection with the parasitic protist *Plasmodium*. While there are four species of *Plasmodium* that can infect humans, the species *Plasmodium falciparum* causes the most dangerous form of malaria with the highest mortality rate. According to the World Health Organization (WHO), there are over 200 million confirmed malaria cases annually, resulting in nearly one million deaths.

In addition, malaria has a negative impact on the wealth of nations and individuals. According to the World Bank, malaria costs Africa about US$12 billion per year and slows gross domestic product (GDP) by over 1% each year. The burden of malaria traps families and communities into deeper poverty by lost productivity and the negative impact on domestic and foreign investment and tourism. Furthermore, malaria greatly affects the structure of society as high mortality rates often afflict the age group under five years old.

The Centers for Disease Control and Prevention in USA notes that although complete elimination of the malaria parasite would be optimal, this is not realistic for most countries endemic for malaria. Improved management of malaria cases is fundamental to control the spreading of malaria.

Rapid diagnostic tests (RDT) are critical for the management of malaria to reduce the morbidity, mortality and transmission of malaria. Commonly-used RTDs for malaria include microscopic, polymerase chain reaction (PCR), and antibody based assays. Microscopic diagnosis of malaria, which is based on the microscopic observation of the malaria parasite in a blood smear, can differentiate various species of *Plasmodium*. PCR based assays can also distinguish various species of *Plasmodium* with high sensitivity. However, both the microscopic and PCR-based diagnostic tests require expensive equipment and highly trained healthcare workers that are generally not available to the majority of the at-risk population in developing countries.

Antibody based assays utilize antibodies for detection of *Plasmodium* antigens. The commonly-used *Plasmodium* antigens for malaria diagnosis include *plasmodium* lactate dehydrogenase (pLDH), histidine rich protein 2 (PfHRP2), and aldolase. While antibody-based rapid diagnostic assays have greatly benefited malaria management, they suffer from significant shortcomings including thermal instability, batch to batch variations, and high cost of production.

Therefore, there is a need for improved methods for malaria diagnosis.

BRIEF SUMMARY

The present invention provides nucleic acid aptamers that bind to *Plasmodium* lactate dehydrogenase and *Plasmodium* histidine rich protein II (referred to herein as "malaria aptamers"), and methods for using these malaria aptamers for the diagnosis and treatment of malaria.

In one embodiment, the present invention provides nucleic acid aptamers that target and bind to two malaria proteins, lactate dehydrogenase and histidine rich protein II, with high specificity and affinity. Aptamers against lactate dehydrogenase can be used for pan-species detection of *Plasmodium*, whilst aptamers against histidine rich protein II can be used for specific detection of *Plasmodium falciparum*. In parallel, these two aptamers can be incorporated into devices both to detect *Plasmodium* and diagnose malaria generally, and to determine whether the malaria is caused specifically by *Plasmodium falciparum*.

The present invention is directed to methods of using malaria aptamers as components of a diagnostic device for the diagnosis of malaria. The method provides specific detection of malaria antigens based on the specificity of binding of the malaria aptamers to the malaria protein targets.

In certain embodiment, the present invention provides formulations comprising a nucleic acid aptamer of the present invention, or a stabilized derivative of such aptamers, or a pharmaceutically acceptable salt thereof. The formulations may comprise any aptamer that binds to *Plasmodium* lactate dehydrogenase or *Plasmodium* histidine-rich protein II or a variant or a fragment thereof.

The present invention also provides methods of using the nucleic acid aptamers of the present invention for the diagnosis or treatment of malaria by specifically binding to and/or inhibiting the function of Plasmodia-encoded proteins.

In terms of diagnostics, the present invention may be used in combination with other diagnostic approaches. In one embodiment, the present invention may administer to a subject an amount of malaria aptamers alone or in combination with other drugs.

In one embodiment, the present invention also provides diagnostic methods of quantifying *Plasmodium* protein levels in a sample. The malaria aptamers may be labeled by a detectable substance, including, but not limited to, fluorescent materials, enzymes, luminescent materials and radioactive materials. Such embodiments of the invention can be used to detect *Plasmodium* protein levels in a biological sample.

BRIEF DESCRIPTION OF THE DRAWINGS

FIG. 3 shows the nucleic acid sequences of embodiments of the aptamers of the present invention. The aptamers bind specifically to *Plasmodium falciparum* lactate dehydrogenase (PfLDH) or histidine rich protein 2 (HRP2). The aptamers are cloned and sequenced from the ssDNA pool after 20 rounds of SELEX (including counter SELEX process by using human LDH and magnetic beads) against *Plasmodium falciparum* PfLDH or against *Plasmodium falciparum* Histidine-rich protein II (HRP2), respectively.

The left panel is the raw calorimetry data and binding isotherm for 2009, and the right panel is the raw calorimetry data and binding isotherm for 2009s (SEQ ID NO:3). PfLDH is titrated with aptamers by serial injections, and the single-binding site model is used to fit the binding isotherms.

Figure 1:
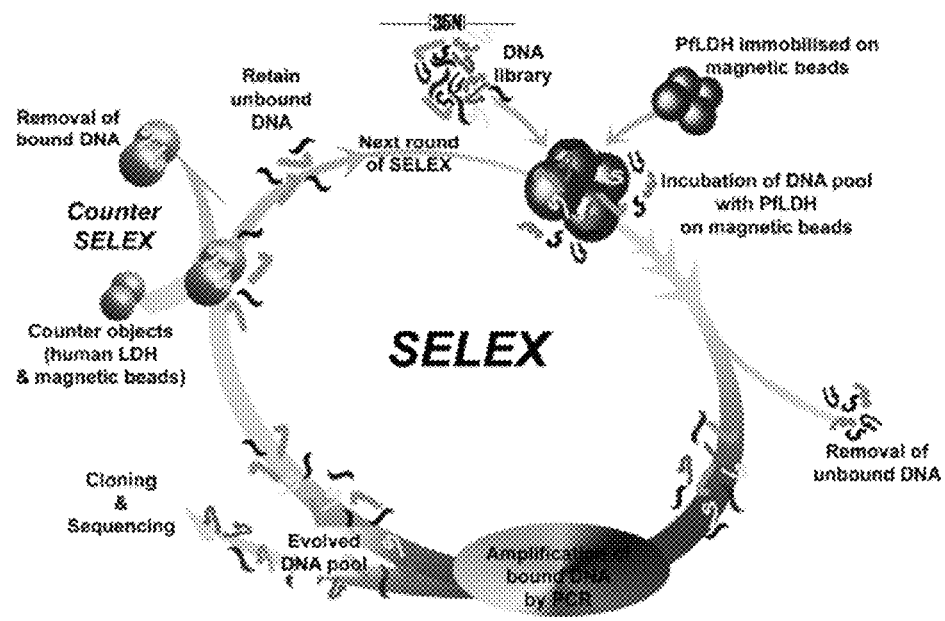
FIG. 1 is an illustration depicting the in vitro selection of aptamers using the "Systematic Evolution of Ligands by Exponential Enrichment" (SELEX™) process.
Figure 2:
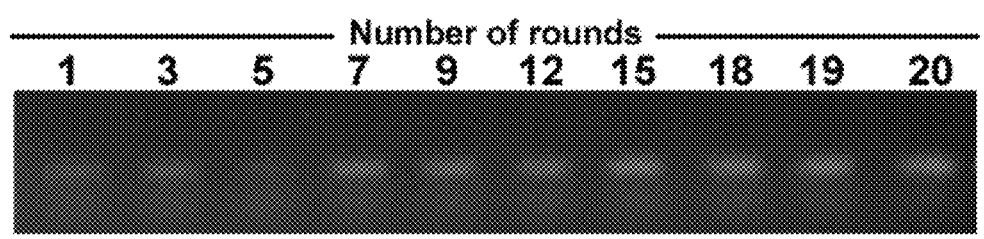
FIG. 2 shows agarose gel analysis of the in vitro selection of LDH aptamers. Samples taken at $1^{st}$, $3^{rd}$, $5^{th}$, $7^{th}$, $9^{th}$, $12^{th}$, $15^{th}$, $18^{th}$, $19^{th}$ and $20^{th}$ rounds.
Figure 4:
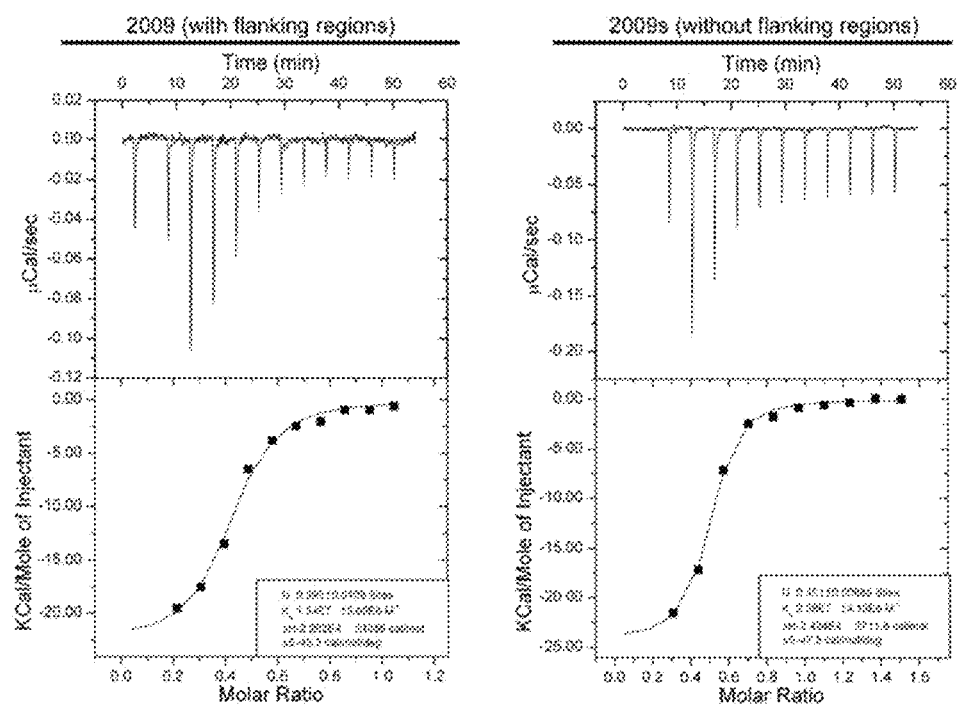
FIG. 4 is a graph showing the comparison between 2009 (the PfLDH aptamer with two 18-mer sequences on each 5' and 3' end) and 2009s using isothermal titration calorimetry.
Figure 5:
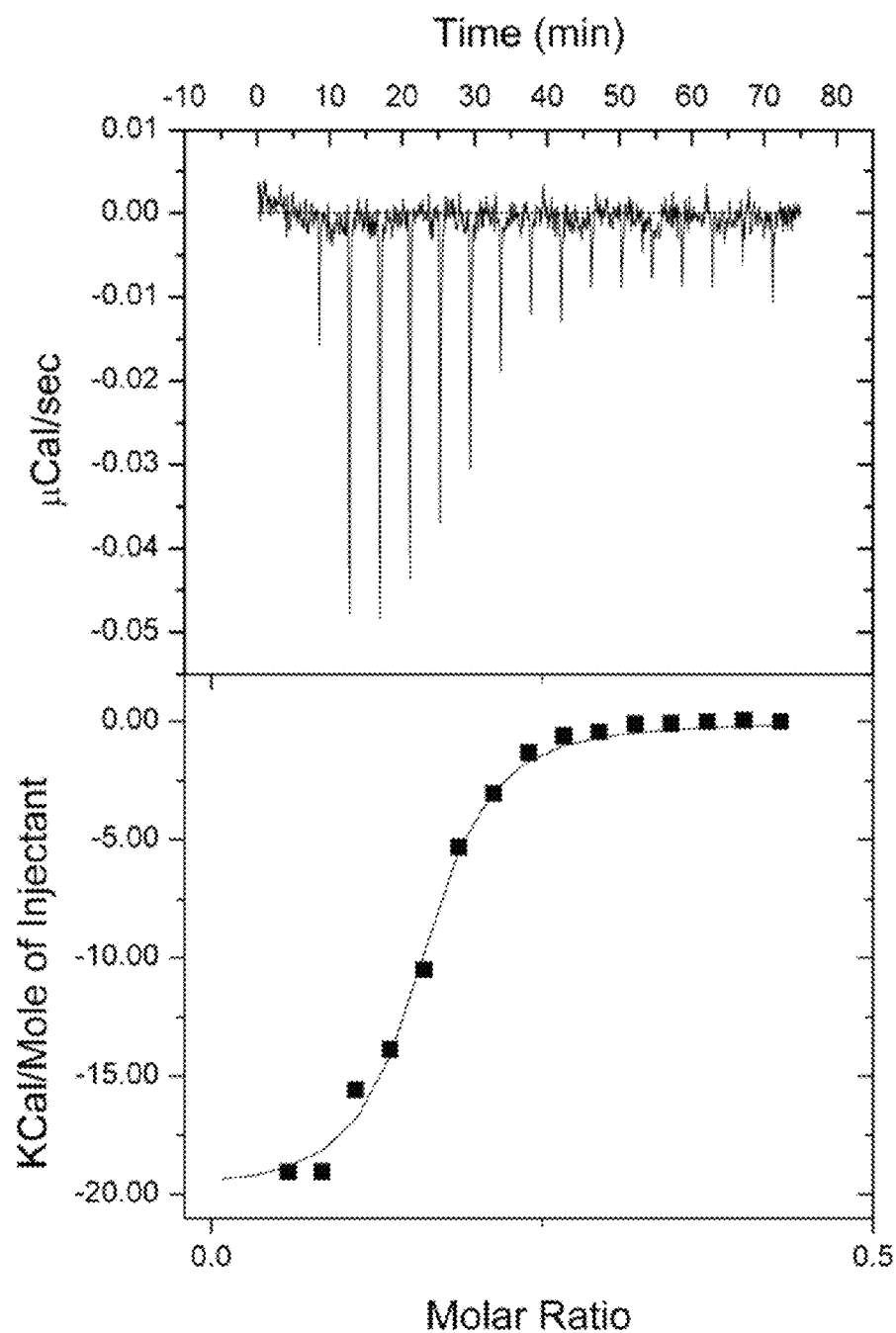

FIG. 5 is a graph showing the result of isothermal titration calorimetry analysis of the binding between PfLDH aptamer (SEQ ID NO:1; 2004s) and recombinant *Plasmodium falciparum* lactate dehydrogenase. The upper panel is the raw calorimetry data of the titration of PfLDH with serial injections of PfLDH aptamer (SEQ ID NO:1; 2004s). The lower panel is the binding isotherm resulting from integration of raw calorimetry data after correction for the heat of aptamer dilution.

Figure 6:
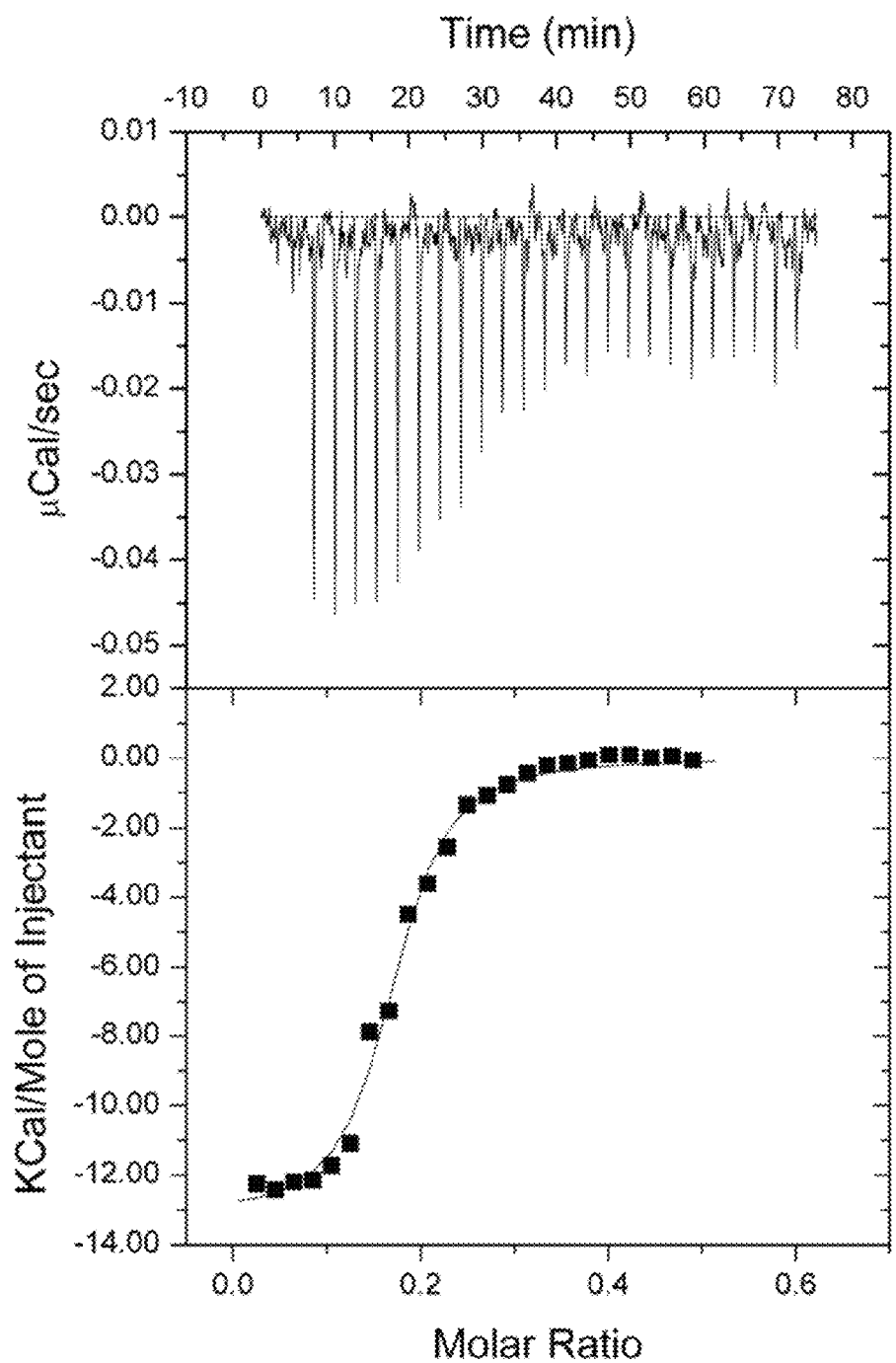

FIG. 6 is a graph showing the result of isothermal titration calorimetry analysis of the binding between PfLDH aptamer (SEQ ID NO:2; 2008s) and recombinant *Plasmodium falciparum* lactate dehydrogenase. The upper panel is the raw calorimetry data of the titration of PfLDH with serial injections of PfLDH aptamer (SEQ ID NO:2; 2008s). The lower panel is the binding isotherm resulting from integration of raw calorimetry data after correction for the heat of aptamer dilution.

Figure 7:
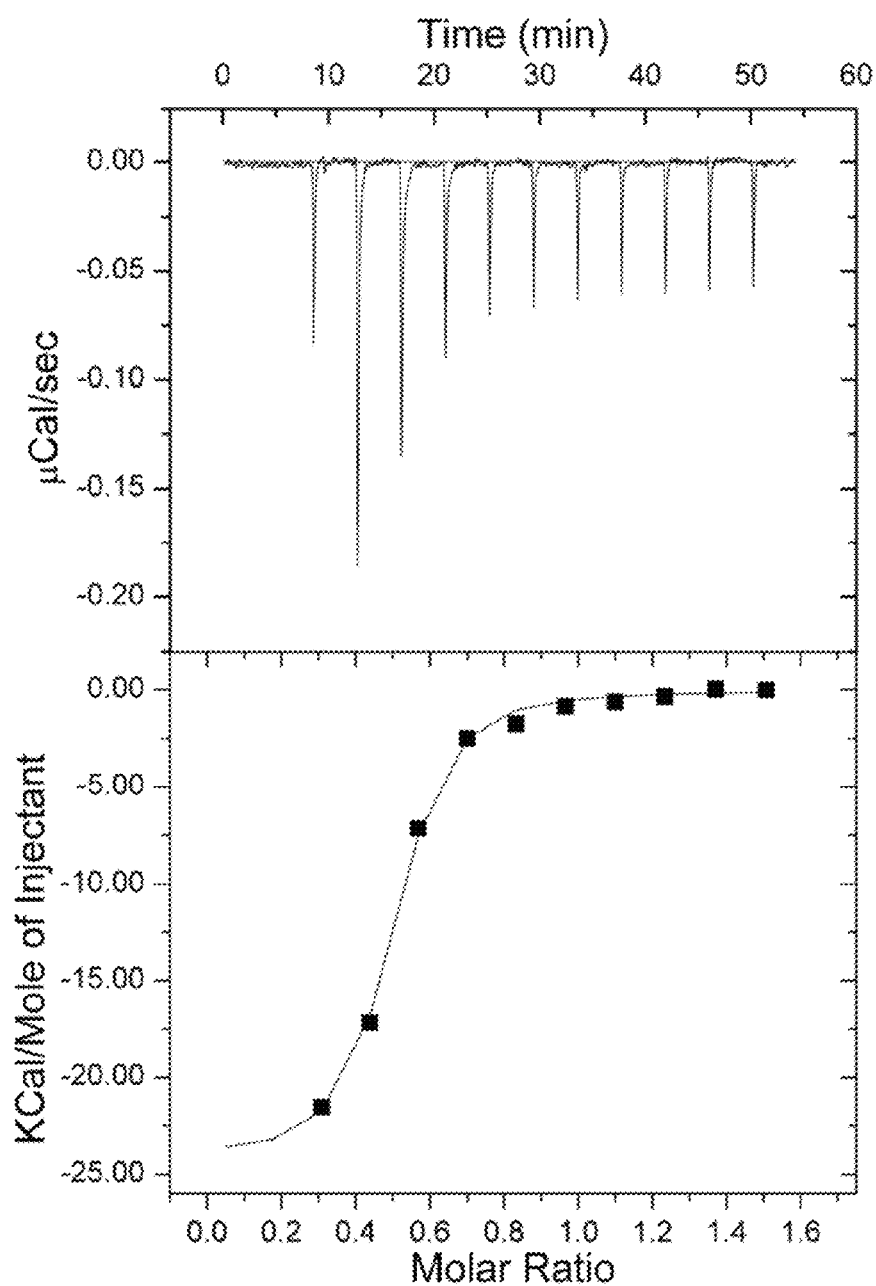

FIG. 7 is a graph showing the result of isothermal titration calorimetry analysis of the binding between PfLDH aptamer (SEQ ID NO:3; 2009s) and recombinant *Plasmodium falciparum* lactate dehydrogenase. The upper panel is the raw calorimetry data of the titration of PfLDH with serial injections of PfLDH aptamer (SEQ ID NO:3; 2009s). The lower panel is the binding isotherm resulting from integration of raw calorimetry data after correction for the heat of aptamer dilution.

Figure 8:
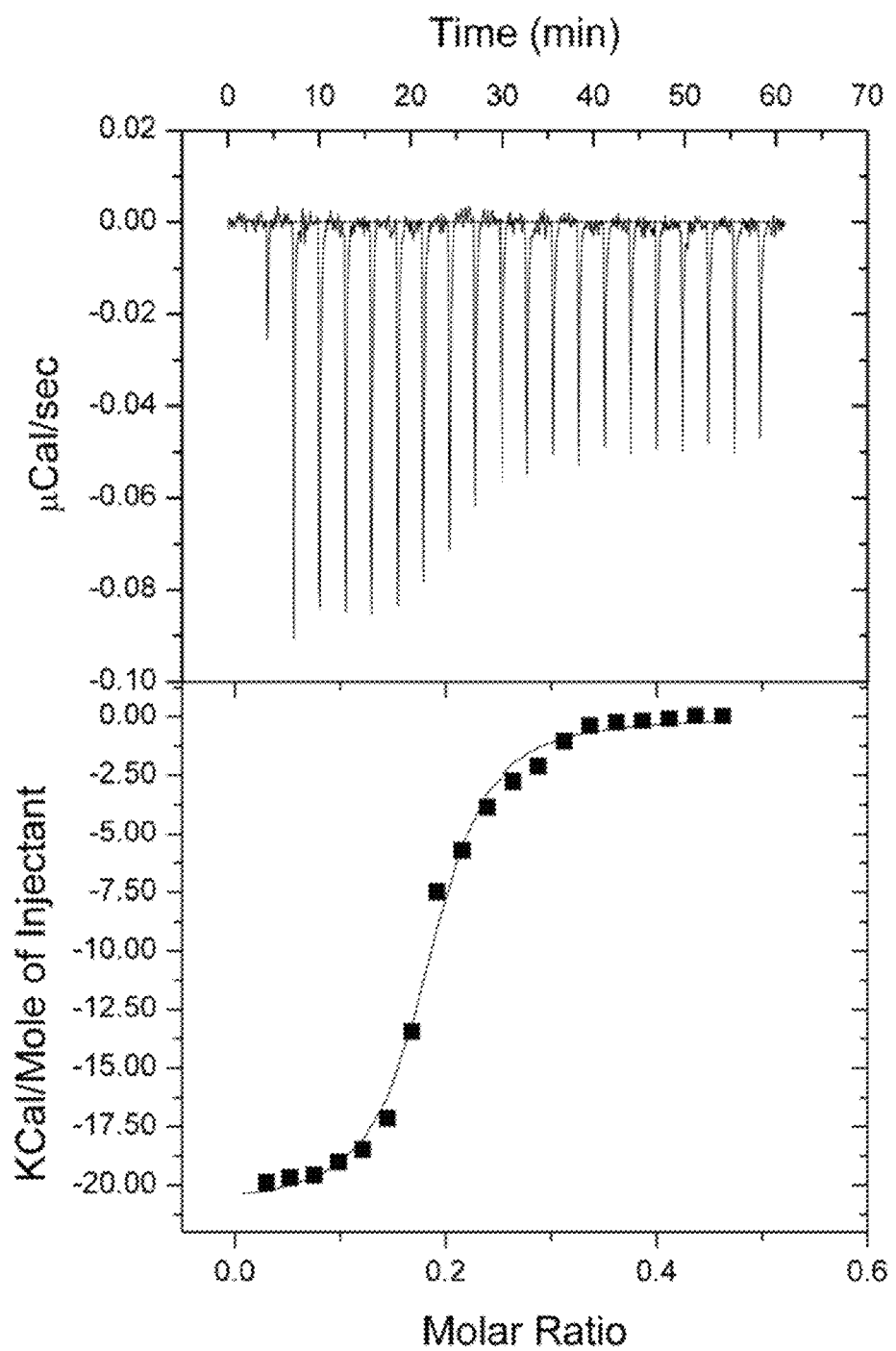

FIG. 8 is a graph showing the result of isothermal titration calorimetry analysis of the binding between PfLDH aptamer (SEQ ID NO:4; 2021s) and recombinant *Plasmodium falciparum* lactate dehydrogenase. The upper panel is the raw calorimetry data of the titration of PfLDH with serial injections of PfLDH aptamer (SEQ ID NO:4; 2021s). The lower panel is the binding isotherm resulting from integration of raw calorimetry data after correction for the heat of aptamer dilution.

FIG. 9 shows the binding of the tetrameric PfLDH to two DNA aptamers of the present invention. (A) Crystal structure of tetrameric LDH in complex with two specific embodiments of the DNA aptamers of the present invention. (B) Structure of a specific embodiment of the DNA aptamer of the present invention in the complexed state, as well as the nucleic acid sequence of that DNA aptamer. (C) Isothermal titration calorimetry titrations for aptamer binding to PfLDH (left) and human LDHA1 and LDHB (right).

FIG. 10 shows the substrate specificity loop at the protein: the aptamer binding: the aptamer binding interface determines the discrimination of the aptamer for PfLDH over hLDH. (A) Direct interactions of DNA aptamer with PfLDH. (B) Discrimination of aptamer binding is due to the difference in the substrate specificity loop. Substrate specificity loops of PfLDH and hLDHB are shown in the (B).

FIG. 11 shows aptamers conjugated to gold nanoparticles for use in molecular diagnostics. (A) Principle of approach. (B) TEM of nanoparticles alone (left), aptamer-conjugated nanoparticles (center) and aptamer-conjugated nanoparticles in the presence of PfLDH (right). (C) Qualitative observation of using nanoparticle to detect PfLDH specifically at 25 ng/µl. (D) Quantitative absorbance of data in (C).

BRIEF DESCRIPTION OF THE SEQUENCES

SEQ ID NO:1 is the nucleic acid sequence of a DNA aptamer binding to *Plasmodium falciparum* lactate dehydrogenase (LDH).

SEQ ID NO:2 is the nucleic acid sequence of a DNA aptamer binding to *Plasmodium falciparum* lactate dehydrogenase (LDH).

SEQ ID NO:3 is the nucleic acid sequence of a DNA aptamer binding to *Plasmodium falciparum* lactate dehydrogenase (LDH).

SEQ ID NO:4 is the nucleic acid sequence of a DNA aptamer binding to *Plasmodium falciparum* lactate dehydrogenase (LDH).

SEQ ID NO:5 is the nucleic acid sequence of a DNA aptamer binding to *Plasmodium falciparum* histidine-rich protein II (HRPII).

SEQ ID NO:6 is the nucleic acid sequence of a DNA aptamer binding to *Plasmodium falciparum* histidine-rich protein II (HRPII).

SEQ ID NO:7 is the nucleic acid sequence of a DNA aptamer binding to *Plasmodium falciparum* histidine-rich protein II (HRPII).

SEQ ID NO:8 is the nucleic acid sequence of a DNA aptamer binding to *Plasmodium falciparum* histidine-rich protein II (HRPII).

SEQ ID NO:9 is the nucleic acid sequence of a DNA aptamer binding to *Plasmodium falciparum* histidine-rich protein II (HRPII).

SEQ ID NO:10 is the nucleic acid sequence of a DNA aptamer binding to *Plasmodium falciparum* histidine-rich protein II (HRPII).

SEQ ID NO:11 is the nucleic acid sequence of a DNA aptamer binding to *Plasmodium falciparum* histidine-rich protein II (HRPII).

SEQ ID NO:12 is the nucleic acid sequence of a primer useful according to the present invention.

SEQ ID NO:13 is the nucleic acid sequence of a primer useful according to the present invention.

SEQ ID NO:14 is the nucleic acid sequence useful according to the present invention.

SEQ ID NO:15 is the nucleic acid sequence of a primer useful according to the present invention.

SEQ ID NO:16 is the nucleic acid sequence of a primer useful according to the present invention.

SEQ ID NO:17 is the nucleic acid sequence of a primer useful according to the present invention.

SEQ ID NO: 18 is the nucleic acid sequence of a primer useful according to the present invention.

SEQ ID NO:19 is the nucleic acid sequence of a primer useful according to the present invention.

SEQ ID NO:20 is the nucleic acid sequence of a primer useful according to the present invention.

DETAILED DESCRIPTION

The present invention provides nucleic acid aptamers binding to *Plasmodium* lactate dehydrogenase (LDH) or *Plasmodium* histidine-rich protein II (HRPII). The nucleic acid aptamers of the present invention can comprise DNA or RNA nucleotides. In one embodiment, the present invention provides DNA aptamers binding to *Plasmodium* lactate dehydrogenase (LDH) or *Plasmodium* histidine-rich protein II (HRPII).

In certain specific embodiments, the present invention provides eleven different sequences of DNA aptamers comprising nucleic acid sequences selected from SEQ ID NOs: 1-11. Four of these aptamers (SEQ ID NOs: 1-4) were selected against *Plasmodium* lactate dehydrogenase and seven of these aptamers (SEQ ID NOs: 5-11) were selected against *Plasmodium* histidine Rich Protein II.

Isothermal titration calorimetry results show tight binding of the aptamers of the present invention to their respective targets (*Plasmodium* lactate dehydrogenase and *Plasmodium* histidine Rich Protein II) (FIGS. 4-8). These aptamers also show negligible binding to control proteins, demonstrating specific binding to the respective targets. In particular, the *Plasmodium* LDH aptamers of the present invention do not bind to human LDH.

The present invention also provides uses of the nucleic acid aptamers of the present invention for rapid and sensitive detection of *Plasmodium* in a sample, as well as for detection of malaria in a subject.

Aptamers Binding to *Plasmodium* LDH and *Plasmodium* HRPII

The present invention provides nucleic acid aptamers binding to *Plasmodium* lactate dehydrogenase (LDH) or *Plasmodium* histidine-rich protein II (HRPII). The nucleic acid aptamers of the present invention can comprise DNA or RNA nucleotides. In one embodiment, the present invention provides DNA aptamers binding to *Plasmodium* lactate dehydrogenase (LDH) or *Plasmodium* histidine-rich protein II (HRPII).

In one embodiment, the present invention provides nucleic acid aptamers binding to, or binding specifically to, *Plasmodium* lactate dehydrogenase (LDH), wherein the aptamer comprises any one of SEQ ID NOs: 1-4:

```
                                       (SEQ ID NO: 1)
5'-ACGCGAGCAGGTGGTAGAATCATAATGGCCTGATC-3'
(2004s);

(SEQ ID NO: 2)
5'-CTGGGCGGTAGAACCATAGTGACCCAGCCGTCTAC-3'
(2008s);

(SEQ ID NO: 3)
5'-TAGGTGGCCAGAAGGTAGAACCATAGTGGTCTGGTA-3'
(2009s);
and (SEQ ID NO: 4)
5'-AGAATGGCGGGAGAGCCTTAGCGACCATTCGTAC-3'
(2021s).
```

In another embodiment, the present invention provides nucleic acid aptamers binding to, or binding specifically to, *Plasmodium* histidine-rich protein II (HRPII), wherein the aptamer comprises any one of SEQ ID NOs: 5-7:

```
                                       (SEQ ID NO: 5)
5'-AGCGCATTCATGCGCTCCCGCTTATGCGGGCGGCCACGTGGAAAC

CCGGTTTCGCTTGTTCTGCTAGCC-3' (2101s);

(SEQ ID NO: 6)
5'-TGCCCACTTATGTTCGCCCCCCCCCTCTTGTTCTC-3' (2105s);

(SEQ ID NO: 7)
5'-GCTTATCCGATGCAGACCCCTTCGGTCCTGCCCTC-3' (2106s);

(SEQ ID NO: 8)
5'-TGGTCATGCCGTTGGGAGTATCATTCCCCGTACGC-3' (2112s);

(SEQ ID NO: 9)
5'-CACTCCACTGAGAACTTGCGAGTGGTCCCATTTTACCTAGCCGTCC

CGCACTGCTGCTTTCTGTGCGGACCGTATC-3' (2115s);

(SEQ ID NO: 10)
5'-CTGGGGGGGTTCTAGGGGGGGGCACTTATCTGCA-3' (2126s);
and
```

```
                                       (SEQ ID NO: 11)
5'-TTATTGGGGGGGTTAGGGGGGGGCTTTTATTCACT-3' (2144s).
```

As shown in the results of isothermal titration calorimetry (FIG. 4), the aptamer with the addition of two 18-mer sequences on both 5' and 3' ends of SEQ ID NO:3 has similar stoichiometry, dissociation constant, and binding affinity to *Plasmodium* LDH (similar binding affinity in nanomolar range), when compared to the aptamer having SEQ ID NO:3.

In certain embodiments, the present invention provides nucleic acid aptamers binding to *Plasmodium* lactate dehydrogenase (LDH), wherein the aptamer comprises a nucleic acid sequence having at least about 80% identity to any of SEQ ID NOs: 1-4, or any percentages higher than 80%, such as, at least 85%, 90%, 92%, 93%, 94%, 95%, or 98%.

In certain embodiments, the present invention provides nucleic acid aptamers binding to *Plasmodium* histidine-rich protein II (HRPII), wherein the aptamer comprises a nucleic acid sequence having at least about 80% identity to any of SEQ ID NOs: 5-11, or any percentages higher than 80%, such as, at least 85%, 90%, 92%, 93%, 94%, 95%, or 98%.

In certain embodiments, the present invention provides nucleic acid aptamers binding to *Plasmodium* lactate dehydrogenase (LDH), wherein the aptamer comprises a nucleic acid sequence with no more than 8, 7, 6, 5, 4, 3, 2 or 1 modifications (such as addition, deletion, substitution) of nucleic acids to any of SEQ ID NOs: 1-4.

In certain embodiments, the present invention provides nucleic acid aptamers binding to *Plasmodium* histidine-rich protein II (HRPII), wherein the aptamer comprises a nucleic acid sequence with no more than 15, 14, 13, 12, 11, 10, 9, 8, 7, 6, 5, 4, 3, 2, or 1 modifications (such as insertion, deletion, substitution) of nucleic acids to SEQ ID NOs: 5-11.

In one embodiment, the present invention provides nucleic acid aptamers binding specifically to *Plasmodium* lactate dehydrogenase (LDH) or *Plasmodium* histidine-rich protein II (HRPII). In one embodiment, the present invention provides nucleic acid aptamers binding specifically to *Plasmodium falciparum* lactate dehydrogenase (LDH) or *Plasmodium falciparum* histidine-rich protein II (HRPII).

"Specific binding" or "specificity" refers to the ability of an aptamer to detectably bind an epitope presented on an antigen, while having relatively little detectable reactivity with other proteins or structures. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

Modification of Aptamer Sequences

Various modifications can be made to the aptamers to reduce exonuclease degradation and increase their lifetimes for diagnostics or for therapy. Modification of the 3' end of the aptamer with inverted thymidine, deoxythymidine nucleotide, and polyethylene glycol (PEG) can reduce degradation of the oligonucleotide aptamer and increases stability of the aptamer. In one embodiment, PEG has an average molecular weight from about 20 to 80 kDa.

Further, the phosphodiester linkages of the deoxyribose-phosphate backbone of the aptamer can also be modified to improve stability.

In one embodiment, the nucleic acid aptamer of the present invention is an oligonucleic acid molecule comprising repeating units of the structure shown in Formula 1. Wavy lines demarcate one nucleotide and/or repeat unit from a neighboring nucleotide and/or repeat unit.

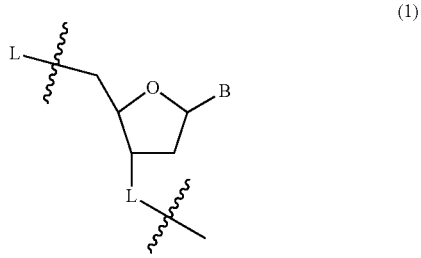

(1)

In one embodiment, each repeat unit of Formula 1 has a deoxyribose moiety linked to one of the common nucleotide bases (B), such as, adenosine, cytidine, guanosine, thymidine, and uridine. The base (B) for each repeating unit is independent from the other repeat units. The nucleotide sequences disclosed herein describe the order of appearance of bases (B) in an aptamer from the repeat unit on the 5' end of the aptamer to the 3' end of the aptamer.

In one embodiment, "L" is a linker group that links the deoxyribose moiety of adjacent repeat units. In the well-known structure of DNA, the L group is a phosphate group $PO_4H$, which can exist as a salt or in a neutral protonated form. The deoxyribose moiety together with the linker group forms the backbone of the aptamer, where the nucleotide base "B" varies independently barriers between repeat units. The majority of the linker groups (L) forming the repeat units of Formula 1 in the aptamer are phosphate groups. As such, a majority of the backbone of the aptamer can be referred to as a deoxyribose-phosphate backbone. Many nuclease enzymes exist that can degrade oligonucleotide molecules without specificity for the specific nucleotide base sequence of the oligonucleotide molecule. Without wishing to be bound by any one particular theory, linker groups "L" other than phosphate can be incorporated into an oligonucleotide or aptamer to prevent degradation by nucleases.

In one embodiment, L can be replaced with a group as shown in Formula 2, where $X_{1-4}$ are independently O or S. $X_2$ and $X_3$ can be bonded to either the 3' carbon or the 5' carbon of a deoxyribose moiety. In one embodiment, $X_1$ is O and $X_4$ is O that can be either protonated or unprotonated. In another embodiment, one or more of $X_2$ and/or $X_3$ is S and $X_1$ and $X_4$ are O, where O can be either protonated or unprotonated. Where one of $X_2$ and/or $X_3$ are S, the aptamer can be referred to as having a thioester linkage in the deoxyribose-phosphate backbone.

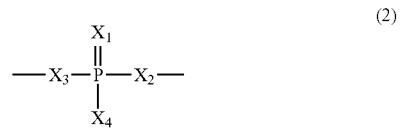

(2)

In another embodiment, the linker group "L" is an amide-containing group as shown in Formula 3, where R can be selected from hydrogen substituted or unsubstituted $C_1$-$C_{10}$ hydrocarbyl group. A "hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In one embodiment, the linker group "L" is a group having Formula 3, and the aptamer comprises amide linkage(s) in the deoxyribose-phosphate backbone. The "NR" group of Formula 3 can be bonded to either the 3' carbon or the 5' carbon of a deoxyribose moiety. In one embodiment, R is methoxymethyl or methoxyethyl.

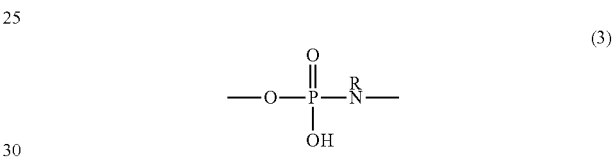

(3)

In some embodiments, the nucleic acid aptamer has from about 14 to about 100 nucleotide bases and/or repeat units, or any number of nucleotide bases or repeating units between 14 to 100, such as between 20 to 50 nucleotide bases and/or repeating units. In some embodiments, the aptamer has from about 14 to about 50 nucleotide bases and/or repeat units. In some embodiments, the aptamer has from about 30 to about 35 nucleotide bases and/or repeat units.

In some embodiments, the aptamer comprises one or more repeating units having the linker "L" selected from Formulae 2-3. In some embodiments of the aptamer of the present invention, the number of repeating units having the linker "L" selected from Formulae 2-3 is between 1 to 15, or any number therebetween such as for example, 1 to 10, 2 to 8, and 3 to 5. Linker groups in repeat units not selected from Formulae 2-3 are phosphate.

In some embodiments of the aptamer of the present invention, about 10% to about 100% (or any percentages therebetween such as about 20% to about 90%, about 30% to about 50%) of the repeat units have the linker "L" selected from Formulae 2-3. In some embodiments of the aptamer of the present invention, about 10% to about 70% of the repeat units have the linker "L" selected from Formulae 2-3. In some embodiments of the aptamer of the present invention, about 10% to about 50% of the repeat units have the linker "L" selected from Formulae 2-3. In some embodiments of the aptamer of the present invention, about 10% to about 30% of the repeat units have the linker "L" selected from Formulae 2-3. In some embodiments of the aptamer of the present invention, about 10% to about 20% of the repeat units have the linker "L" selected from Formulae 2-3. Linker groups in repeat units not selected from Formulae 2-3 are phosphate.

Various nucleases are exonucleases that degrade oligonucleotides from the 5' or 3' end. As such, in one embodiment a linker group L selected from Formulae 2-3 is located within about repeat units from the 5' or the 3' end of the aptamer. In another embodiment, a linker group L selected from Formulae 2-3 is located within about 3 repeat units from the 5' or the 3' end of the aptamer. In yet another embodiment, a linker group L selected from Formulae 2-3 is part of the repeat unit on the 5' or the 3' end of the aptamer.

Degradation of the aptamers can also be reduced by the inclusion of modified nucleotide bases (B). The pyrimidine nucleotide bases, cytosine, thymine and uracil can be replaced with alkylated pyrimidines. Examples of alkylated pyrimidines include pseudoisocytosine; N4,N4-ethanocytosine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; 1-methylpseudouracil; 3-methylcytosine; 5-methylcytosine; 5-methylaminomethyl uracil; 5-methoxy amino methyl-2-thiouracil; 5-methoxycarbonylmethyluracil; 5-methoxyuracil; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; 2-thiocytosine; 5-propyluracil; 5-propylcytosine; 5-ethyluracil; 5-ethylcytosine; 5-butyluracil; 5-pentyluracil; 5-pentylcytosine; methylpseudouracil; and 1-methylcytosine. The purine nucleotide bases, adenine and guanine, can be replaced by alkylated purines. Examples alkylated purines include 8-hydroxy-N6-methyladenine; inosine; N6-isopentyl-adenine; 1-methyladenine; 1-methylguanine; 2,2-dimethylguanine; 2-methyladenine; 2-methylguanine; N6-methyladenine; 7-methylguanine; 2-methylthio-N6-isopentenyladenine; and 1-methylguanine.

In one embodiment, at least one deoxyribose or ribose of the nucleic acid aptamer is replaced with a morpholine ring. In one embodiment, at least one phosphorothioate or phosphodiester linkage of the nucleic acid aptamer is replaced with phosphorodiamidate.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and % or thio groups. Sequences containing nucleotide substitutions, deletions, and/or insertions can be prepared and tested using standard techniques known in the art.

Detection of *Plasmodium* Infections

The present invention also provides methods for diagnosis of malaria and for detection of *Plasmodium* (such as *Plasmodium falciparum*) in a sample.

In one embodiment, the method for diagnosing *Plasmodium* infection or malaria in a subject comprises:

obtaining a biological sample from a subject;

contacting the biological sample with a nucleic acid aptamer comprising any one of SEQ ID NOs: 1-11, or a sequence having at least 85% identity to any one of SEQ ID NOs: 1-11;

determining the formation of the binding complex between the nucleic acid aptamer and *Plasmodium* lactate dehydrogenase (LDH) or *Plasmodium* histidine-rich protein II (HRPII), wherein the presence of the binding complex indicates that the subject has *Plasmodium* infection.

In one embodiment, the method comprises contacting a sample with a nucleic acid aptamer comprising any one of SEQ ID NOs: 1-4, or a sequence having at least 85% identity to any one of SEQ ID NOs: 1-4, and determining the formation of the binding complex between the nucleic acid aptamer and *Plasmodium* lactate dehydrogenase (LDH).

In another embodiment, the present invention provides a method for detecting the presence of *Plasmodium* in a sample, wherein the method comprises:

contacting a sample with a nucleic acid aptamer comprising any one of SEQ ID NOs: 1-11, or a sequence having at least 85% identity to any one of SEQ ID NOs: 1-11;

determining the formation of the binding complex between the nucleic acid aptamer and *Plasmodium* lactate dehydrogenase (LDH) or *Plasmodium* histidine-rich protein II (HRPII), wherein the formation of the binding complex indicates the presence of *Plasmodium* in the sample.

In a further embodiment, the method further determines the concentration or amount of *Plasmodium* in the sample comprising determining the concentration or amount of the binding complex between the aptamer of the present invention and *Plasmodium* lactate dehydrogenase (LDH) or *Plasmodium* histidine-rich protein II (HRPII).

In another embodiment, the method comprises contacting a sample with a nucleic acid aptamer comprising any one of SEQ ID NOs: 5-11, or a sequence having at least 85% identity to any one of SEQ ID NOs: 5-11, and determining the formation of the binding complex between the nucleic acid aptamer and *Plasmodium* histidine-rich protein II (HRPII).

Aptamers against lactate dehydrogenase can be used for pan-species detection of *Plasmodium*, whilst aptamers against histidine rich protein II can be used for specific detection of *Plasmodium falciparum*.

The term "subject," as used herein, describes an organism, including mammals such as primates. Mammalian species that can benefit from the subject methods include, but are not limited to, apes, chimpanzees, orangutans, humans, monkeys; and domesticated and/or laboratory animals such as dogs, cats, horses, cattle, pigs, sheep, goats, chickens, mice, rats, guinea pigs, and hamsters. Typically, the subject is a human.

In certain embodiments, the present invention can be used to detect the presence of *Plasmodium* species including, but not limited to, *Plasmodium falciparum*, *Plasmodium yoelii*, *Plasmodium knowlesi*, *Plasmodium brasilaneum*, *Plasmodium ovale*, *Plasmodium chaboudi*, *Plasmodium vivax*, *Plasmodium malariae*, *Plasmodium berghei*, *Plasmodium reichenowi*, and *Plasmodium gallinaceum*.

In one specific embodiment, the present invention can be used to detect the presence of *Plasmodium falciparum* in a sample, as well as to diagnose whether a subject has malaria caused by *Plasmodium falciparum* infection.

The aptamers of the present invention can be labeled with a detectable substance and localized in biological samples based upon the presence of the detectable substance. Examples of detectable substances include, but are not limited to, the following radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags).

The terms "detecting" or "detect" include assaying or otherwise establishing the presence or absence of the target *Plasmodium* LDH or HRPII, or combinations of agent bound targets.

A "sample" (biological sample) can be any composition of matter of interest from a human or non-human subject, in any physical state (e.g., solid, liquid, semi-solid, vapor) and of any complexity. Preferably, the sample is a fluid (biological fluid). Samples preferably include human samples. The sample may be contained within a test tube, culture vessel, multi-well plate, or any other container or supporting substrate. The sample can be, for example, a cell culture or human tissue.

The term "biological sample," as used herein, includes but is not limited to a sample containing tissues, cells, and/or biological fluids isolated from a subject. Examples of biological samples include but, are not limited to, tissues, cells, biopsies, blood, lymph, serum, plasma, urine, saliva, and tears. In various embodiments, biological samples are obtained from, or derived from, blood, including plasma, serum, and blood cells.

In certain embodiment, the detection and diagnostic assays of the present invention can be performed using assay devices, such as a lateral flow device, and a device for colorimetric assays.

Kits

In one aspect, the present invention includes kits comprising the required elements for detection of *Plasmodium* in a sample. In one embodiment, the kit comprises one or more nucleic acid aptamers of the present invention.

Preferably, the kits comprise a container for collecting samples and an agent for detecting the presence of *Plasmodium* lactate dehydrogenase (LDH) or *Plasmodium* histidine-rich protein II (HRPII). Other components of the kit may include but are not limited to, means for collecting biological samples, means for labeling the detecting agent (binding agent), solid support, buffers, labels, tags, and preservatives. The kit can also contain a solid support such as microtiter multi-well plates, standards, assay diluent, wash buffer, adhesive plate covers, and/or instructions for carrying out a method of the invention using the kit. In one embodiment, the kit includes one or protease inhibitors (e.g., a protease inhibitor cocktail) to be applied to the biological sample to be assayed (such as blood or urine).

As used herein, the terms "label" and "tag" refer to substances that may confer a detectable signal, and include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc., which may be further labeled with a dye, catalyst or other detectable group.

As used herein, the term "conjugate" refers to a compound comprising two or more molecules bound together, optionally through a linking group, to form a single structure. The binding can be made by a direct connection (e.g., a chemical bond) between the molecules or by use of a linking group.

As used herein, the terms solid "support", "substrate", and "surface" refer to a solid phase which is a porous or non-porous water insoluble material that can have any of a number of shapes, such as strip, rod, particle, beads, or multi-welled plate. In some embodiments, the support has a fixed organizational support matrix that preferably functions as an organization matrix, such as a microtiter tray. Solid support materials include, but are not limited to, cellulose, polysaccharide such as Sephadex, glass, polyacryloylmorpholide, silica, controlled pore glass (CPG), polystyrene, polystyrene/latex, polyethylene such as ultrahigh molecular weight polyethylene (UPE), polyamide, polyvinylidine fluoride (PVDF), polytetrafluoroethylene (PTFE; TEFLON), carboxyl modified teflon, nylon, nitrocellulose, and metals and alloys such as gold, platinum and palladium. The solid support can be biological, non-biological, organic, inorganic, or a combination of any of these, existing as particles, strands, precipitates, gels, sheets, pads, cards, strips, dipsticks, test strips, tubing, spheres, containers, capillaries, pads, slices, films, plates, slides, etc., depending upon the particular application. Preferably, the solid support is planar in shape, to facilitate contact with a biological sample such as urine, whole blood, plasma, serum, peritoneal fluid, or ascites fluid. Other suitable solid support materials will be readily apparent to those of skill in the art. The solid support can be a membrane, with or without a backing (e.g., polystyrene or polyester card backing), such as those available from Millipore Corp. (Bedford, Mass.), e.g., Hi-Flow™ Plus membrane cards. The surface of the solid support may contain reactive groups, such as carboxyl, amino, hydroxyl, thiol, or the like for the attachment of nucleic acids, proteins, etc. Surfaces on the solid support will sometimes, though not always, be composed of the same material as the support. Thus, the surface can be composed of any of a wide variety of materials, such as polymers, plastics, resins, polysaccharides, silica or silica-based materials, carbon, metals, inorganic glasses, membranes, or any of the aforementioned support materials (e.g., as a layer or coating).

EXAMPLES

Following are examples that illustrate procedures and embodiments for practicing the invention. The examples should not be construed as limiting.

Example 1

Properties of Aptamers that Bind to *Plasmodium* LDH and HRPII

The thermodynamics of the interaction between the claimed aptamers and their targets were studied by using isothermal titration calorimetry. As shown in FIGS. 4-8, the aptamers claimed were observed to specifically bind with nanomolar affinity ($K_d$) to their targets without binding to controls.

In the upper panel of FIG. 5, an exothermic heat pulse was observed after each injection of 2004s to PfLDH solution. Using a single site binding model to fit the data then the result shows the stoichiometry of the 2004s-PfLDH complex is 0.152±0.003 sites, which indicates more than one 2004s may bind per PfLDH molecule in solution at 25° C.

In the upper panel of FIG. 6, an exothermic heat pulse was observed after each injection of 2008s to PfLDH solution. Using a single site binding model to fit the data then the result shows the stoichiometry of 2008s-PfLDH complex is 0.166±0.003 sites, which indicates more than one 2008s may bind per PfLDH molecule in solution at 25° C.

In the upper panel of FIG. 7, an exothermic heat pulse was observed after each injection of 2009s to PfLDH solution. Using a single site binding model to fit the data then the result shows the stoichiometry of 2009s-PfLDH complex is 0.451±0.007 sites, which indicates two 2009s molecules may bind per PfLDH molecule in solution at 25° C.

In the upper panel of FIG. 8, an exothermic heat pulse was observed after each injection of 2021s to PfLDH solution. Using a single site binding model fit the data then the result shows the stoichiometry of 2021s-PfLDH complex is 0.177±0.003 sites, which indicates more than one 2021s may bind per PfLDH molecule in solution at 25° C.

Materials and Methods

The present invention describes aptamers that bind to PfLDH and HRP. PfLDH was obtained by molecular cloning of cDNA of PfLDH from *Plasmodium falciparum* 3D7 cDNA library. The coding region of PfLDH was amplified by PCR with the forward primer 5'-ATTATTGCTAGC ATGGCACCAAAAGCAAAAATCGTTTTAGTTG-3' (SEQ ID NO: 12) and the reverse primer 5'-ATTATTCTC-GAGTTAAGCTAATGCCTTCATTCTCTTAGTTTCA-3' (SEQ ID NO:13). The PCR product was digested with NheI/XhoI, purified by gel purification and ligated to the NheI/XhoI digested pET-28a vector to become the expression plasmid pET28a-PfLDH.

PfLDH was heterologously expressed in *Escherichia coli* BL21(DE3) pLysS. pET28a-PfLDH was transformed into *Escherichia coli* BL21(DE3) pLysS cells for recombinant protein expression. An overnight culture was prepared by inoculating a single colony into LB medium with 50 µg/mL of kanamycin, and followed by incubating in 37° C. overnight. For PfLDH expression, the overnight culture was diluted in LB medium in 1:50 ratio and incubated at 37° C. until $OD_{600}$ reached 0.5, then isopropyl-D-thiogalactopyranoside (IPTG) was added to the culture to a final concentration of 0.5 mM to induce the PfLDH expression. The induced culture was further incubated in room temperature for 4 hours and cells were harvested by centrifugation.

For the extraction of recombinant PfLDH from *Escherichia coli* BL21 (DE3) pLysS cells, the harvested cells were suspended into lysis buffer (50 mM Tris-HCl, pH 7.5, 0.3 M NaCl, 20 mM imidazole with protease inhibitor and Benzonase) in 1:50 of lysis buffer to cell culture ratio. The cell suspension was incubated on ice for 30 minutes and followed by sonicating for 10 minutes in 9 seconds on and 5 seconds off cycle. The bacterial cell lysate was centrifuged at 18000×g for 20 minutes and the supernatant, soluble protein extract, was collected for PfLDH purification.

Recombinant PfLDH was purified by affinity chromatography. The soluble protein extract was loaded on nickel affinity column and PfLDH was eluted by different 150 mM of imidazole in 50 mM Tris-HCl, pH7.5, 0.3 M NaCl.

PfLDH aptamers were selected by SELEX performed on PfLDH immobilised magnetic beads and counter SELEX performed on human lactate dehydrogenase immobilised magnetic beads and the naked magnetic beads. The selection of PfLDH aptamers was started by incubating a single-stranded DNA (ssDNA) library containing 35mer random region flanked by two 18mer priming regions (5'-CGTACG-GTCGACGCTAGC-[N35]-CACGTGGAGCTCGGATCC-3') (SEQ ID NO:14) with the PfLDH immobilised magnetic beads. After incubation, the unbound species were removed and the ssDNA-PfLDH-magnetic beads complexes were suspended in 10 µL of water.

PCR was carried out for the amplification of PfLDH bound species. The reaction mixtures for PCR contained 10 µL Pwo SuperYield PCR buffer, 10 mM dNTPs, 20 mM forward primer (5'-CGTACGGTCGACGCTAGC-3') (SEQ ID NO:15), 20 mM reverse primer (5'-biotin-GGATC-CGAGCTCCACGTG-3') (SEQ ID NO:16), 10 µL of magnetic beads suspension, 2.5 U Pwo SuperYield DNA polymerase and water to a final volume of 100 µL. PCR conditions were denaturation at 95° C. for 15 seconds, annealing at 50° C. for 30 seconds and elongation at 72° C. for 15 seconds for 10 cycles.

PCR products were collected and incubated with streptavidin magnetic beads. Unbiotinylated ssDNAs were eluted by adding 100 mM NaOH. The first to third round of selections, eluted ssDNAs were concentrated by ethanol precipitation whereas QIAquick gel extraction kit was used for the following rounds. The yielded ssDNA pool was used for the next round of selection. Counter selections by using naked magnetic beads were included in the forth and seventh rounds, hLDHA1 immobilised magnetic beads were included in sixth and tenth rounds and hLDHB immobilised magnetic beads were included in fifth and ninth rounds. Ultimately, the ssDNA pool from the twentieth round was cloned and the colonies were picked for sequencing.

A similar approach was taken for the expression, purification and selection of aptamers against HRP2.

For isothermal titration calorimetry, PfLDH aptamers and PfLDH were dialysed in 25 mM Tris-HCl, pH 7.5 containing 0.1 M NaCl and 20 mM imidazole. All the buffers, protein and aptamers were degassed for 10 minutes at 25° C. prior to ITC experiments. All the experiments were performed in 25 mM Tris-HCl, pH 7.5 containing 0.1 M NaCl and 20 mM imidazole at 25° C. using $iTC_{200}$ microcalorimeter (MicroCal Inc.). ITC experiment was carried out by injecting PfLDH aptamer into PfLDH. The ITC data were analysed by using Origin v7.0 software (MicroCal Inc.) to integrate the titration curves for extracting the thermodynamic parameters, stoichiometry (N), equilibrium association constant $[K_a(=K_d^{-1})]$ and the binging enthalpy ($\Delta H$).

A similar approach was taken for the investigation of the binding of aptamers to HRPII.

Example 2

Structural Basis of DNA Aptamer Recognition of *Plasmodium* Lactate Dehydrogenase This Example shows the crystal structure and application of one embodiment of a DNA aptamer against a malaria panspecies diagnostic target, *Plasmodium falciparum* lactate dehydrogenase (PfLDH). This example also shows a new mechanism of molecular recognition of *Plasmodium falciparum* lactate dehydrogenase (PfLDH) by the hairpin DNA aptamer of the present invention.

PfLDH and two related human homologues hLDHA1 and hLDHB were cloned, expressed in *E. coli* and purified. DNA aptamers were selected from a pool with a 35-base random region against purified PfLDH and counterselected to remove aptamers bound to the closely related human homologues hLDHA1 and hLDHB. After 20 rounds of selection, 51 sequences were obtained and aligned, revealing the presence of conserved sequence signatures and motifs. A number of these aptamers were observed to specifically bind to PfLDH (the most promising with Kd in the range 20-50 nM) without binding to hLDHA1 and hLDHB, as determined by isothermal titration calorimetry (FIG. 9c), electrophoretic mobility shift assay, and surface plasmon resonance (SPR) spectroscopy.

A single DNA aptamer which showed significant promise (2008s) (SEQ ID NO:2) in the three binding assays (with sequence shown in FIG. 9b) was taken forward for structural analysis.

Figure 9A:
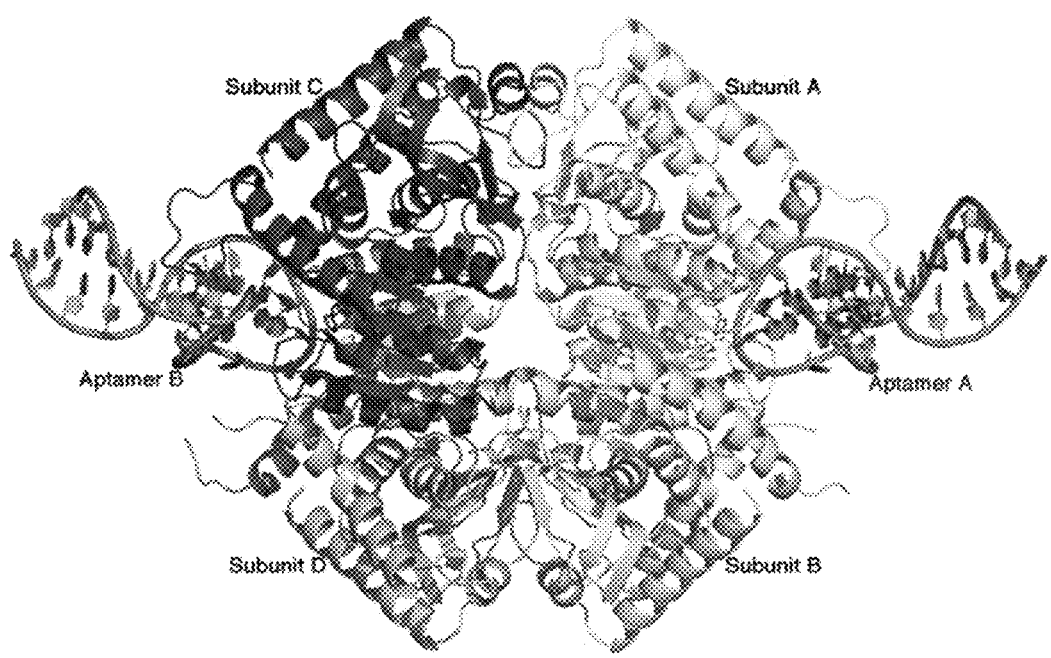

The crystal structure of the PfLDH: aptamer complex was determined by X-ray crystallography (FIG. 9a). The four molecules of PfLDH in the asymmetric unit are organized into a tetramer with characteristic 222 symmetry, similar to previously determined PfLDH X-ray crystallographic structures.

Each of the two ssDNA aptamers were seen bound to the Q-axis dimers formed by molecules A and B (or molecules C and D), spanning across the large cofactor domains of the two juxtaposed monomers.

Figure 9B:
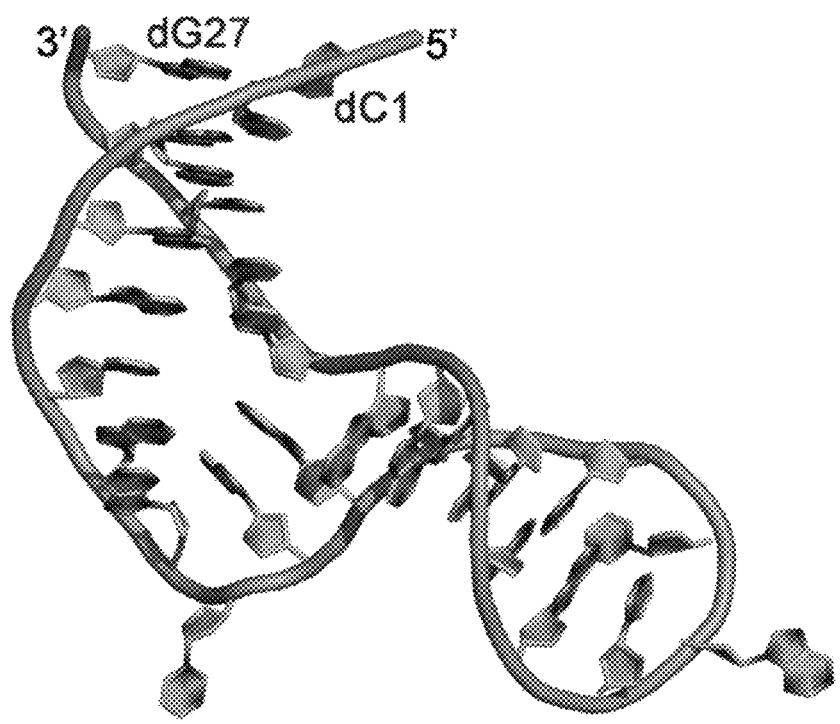
Figure 9C:
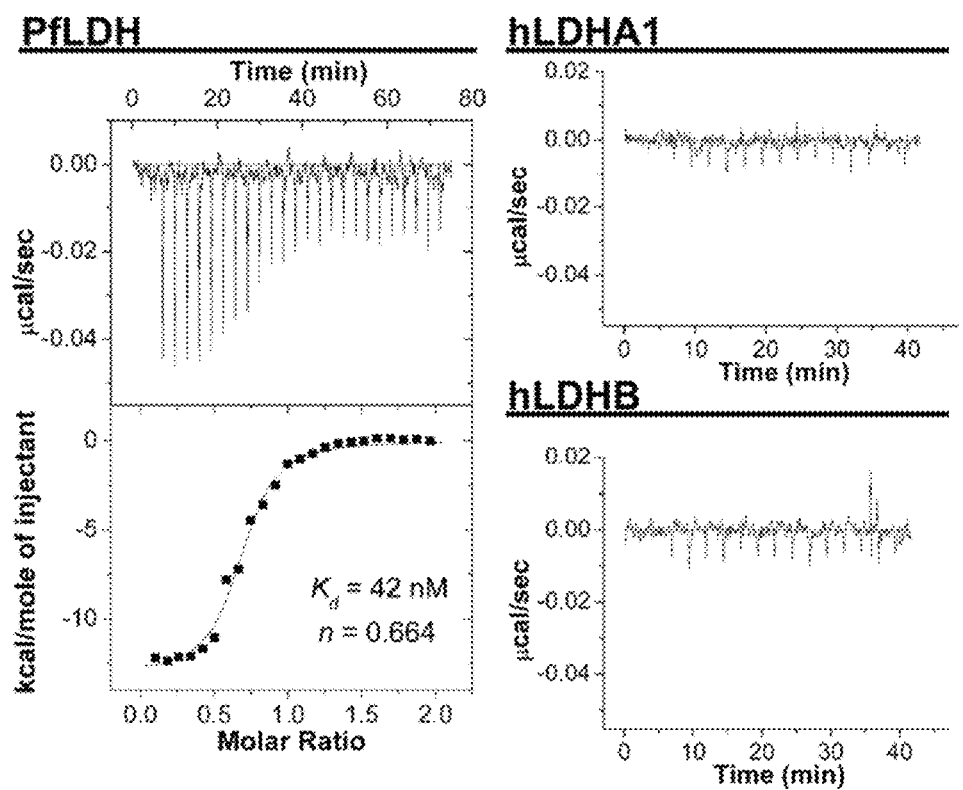

The aptamer did not form a G-quaduplex structure, but showed a hairpin structure (FIG. 9b). Clear electron density was observed for the first 27 bases of both aptamers in the asymmetric unit; no electron density was observed beyond the hairpin structure for the last 8 bases at the 3' end of the aptamer, probably because the aptamer tail is disordered. The global fold of the aptamer adopted a distorted hairpin structure with a $C^{15}A^{16}T^{17}A^{18}$ apical tetraloop, an asymmetric internal loop with six bases in one strand ($C^6G^7G^8T^9A^{10}G^{11}$) and one base in the other ($A^{22}$), and a terminal B-form helix. The aptamer contains seven Watson-Crick type base-pairs, five of which form the terminal B-form helical stem DNA duplex. The remaining two Watson-Crick type base pairs, together with non-canonical base pairing between $A^{12}$ and $G^{21}$, form the DNA duplex flanking between the internal loop and apical loop. Similar to the terminal B-helical stem, this short duplex assumes B-helical geometry. The two B-helices are oriented in an ~140° angle, resulting in an overall bent shape for the DNA aptamer. $C^6$ of the internal loop is involved in stacking interaction with its neighbors, $G^5$ of the stem B-helix. As a result, $C^6$, $G^7$ and $G^8$ of the internal loop remain within the stem B-helix as they continuously stack. $G^7$ and $A^{10}$ form a non-canonical base pair in the internal loop. $T^9$ is flipped out of the internal loop and is engaged in aptamer: PfLDH interactions as described below. In the apical tetraloop, both $T^{17}$ and $A^{18}$ are involved in stacking interactions and remain in the helical axis of the short duplex flanking the apical loop and internal loop. $C^{15}$ and $A^{16}$ are flipped out of the apical loop, the position of $C^{15}$ is stabilised by interaction of N4 with the backbone phosphate of $C^{14}$, while $A^{16}$ is involved in indirect interactions with PfLDH via waters.

Figure 10A:
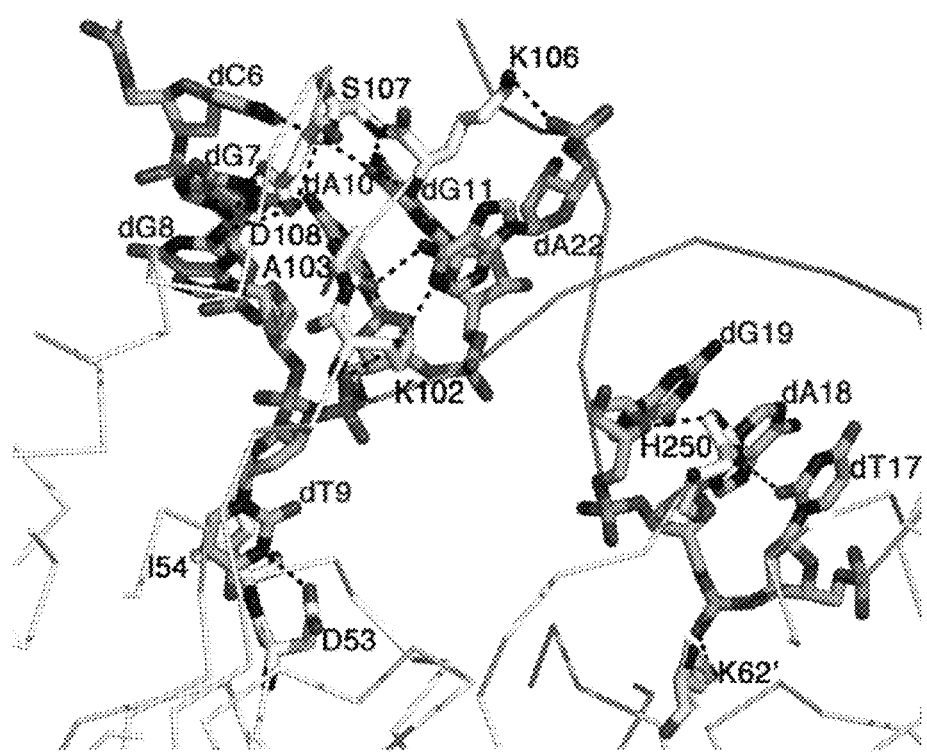

Each aptamer interacts through extensive salt bridges with the cofactor binding sites of two PfLDH molecules of the Q-axis dimer (FIG. 10a). The interface between the aptamer and PfLDH buries a solvent-accessible surface of 1276 Å2 on the aptamer and 895 Å2 and 394 Å2 for molecules A/C and B/D of PfLDH respectively. The aptamer interacts with the substrate specificity loop at the tip of the cofactor binding sites of the two adjacent PfLDH molecules via distinct regions. Molecule A/C interacts with the internal loop whilst molecule B/D interacts with the apical tetraloop.

The aptamer interacts with Molecule A of the PfLDH dimer via the internal loop. The bases $C^6$, $G^7$, $G^8$, $G^{11}$ and $A^{22}$ of the internal loop of the DNA aptamer form extensive base interactions with residues 102A-108A of the extended substrate specificity loop, backbone contacts are also seen with Lys102A and Lys106A forming contacts with the phosphates of $A^{10}$ and $A^{22}$ respectively. The flipped base $T^9$ extends away from the bent hairpin structure into the adenine end of the NADH binding cleft and is stabilized by hydrogen bonds between N3 of the $T^9$ base and the sidechain of Asp53A, and O4 of the $T^9$ base with the amino nitrogen of Ile54A.

Compared to the interaction of the internal loop and Molecule A of PfLDH, the interaction of the apical tetraloop with Molecule B of PfLDH is less extensive and involves indirect contacts via water molecules. Direct backbone contacts are observed with phosphate groups of A18 and G19 of the tetraloop interacting with the sidechains of Lys62B and His250B of the NADH binding cleft. Similar to T9 in the internal loop, the flipped base A16 extends into the adenine end of the NADH binding cleft of molecule B. However, instead of direct interactions with the protein, the position of A16 of the apical loop is stabilised via indirect interactions with the protein via water molecules (FIG. 10a).

Figure 10B:
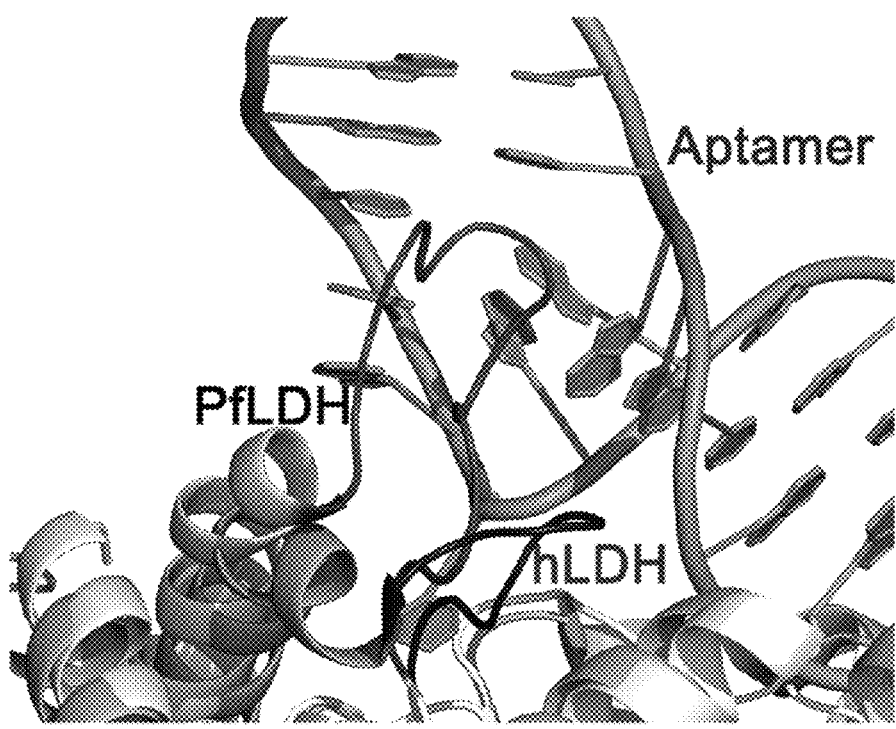

The extensive interaction of this aptamer to the unique extended substrate specificity loop of PfLDH (amino acids 102-108) contributes to the high specificity of aptamer binding to PfLDH and not human LDH. Indeed, superposition of human LDHB (PDB accession code: IT2F) with our PfLDH: aptamer structure revealed that human LDH lacks the extension at the substrate specificity loop, resulting in an inability to reach the aptamer (FIG. 10b). Thus, binding of the aptamer to human LDH would not occur, which both proves that the counter selection strategy was successful and provides a structural explanation for the specificities determined in our binding assays.

Figure 11A:
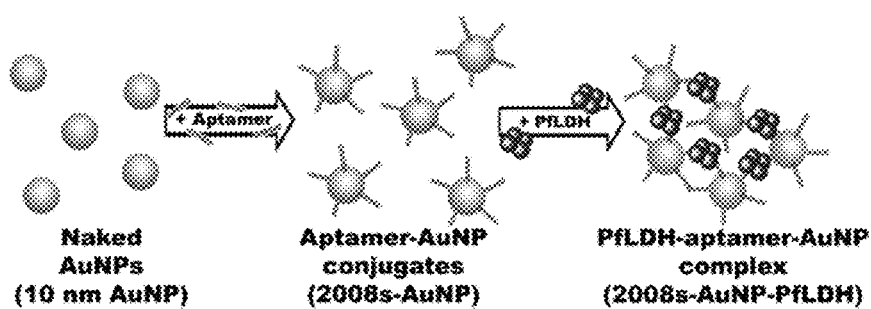
Figure 11B:
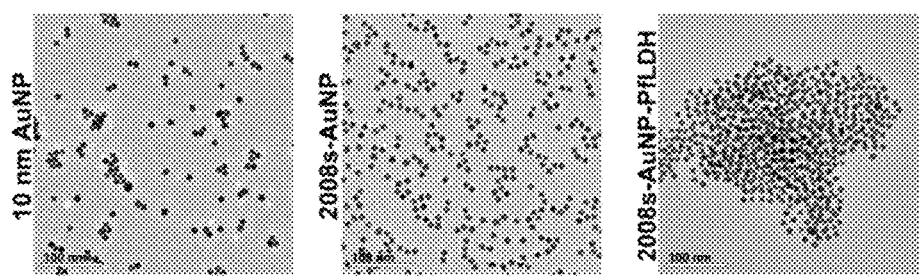
Figure 11C:
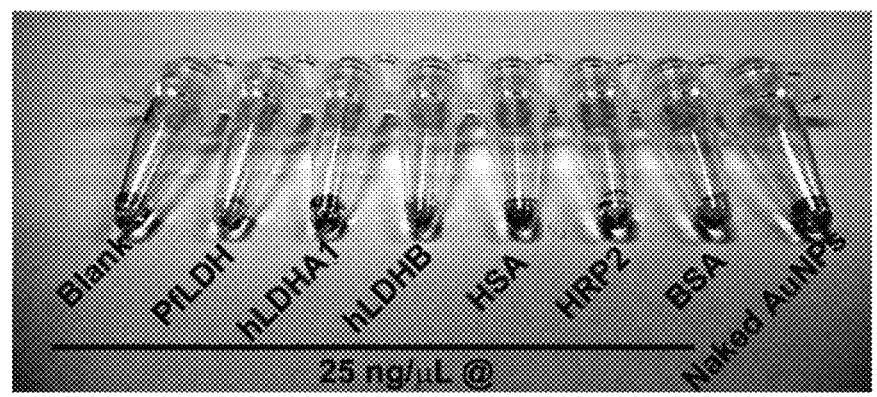
Figure 11D:
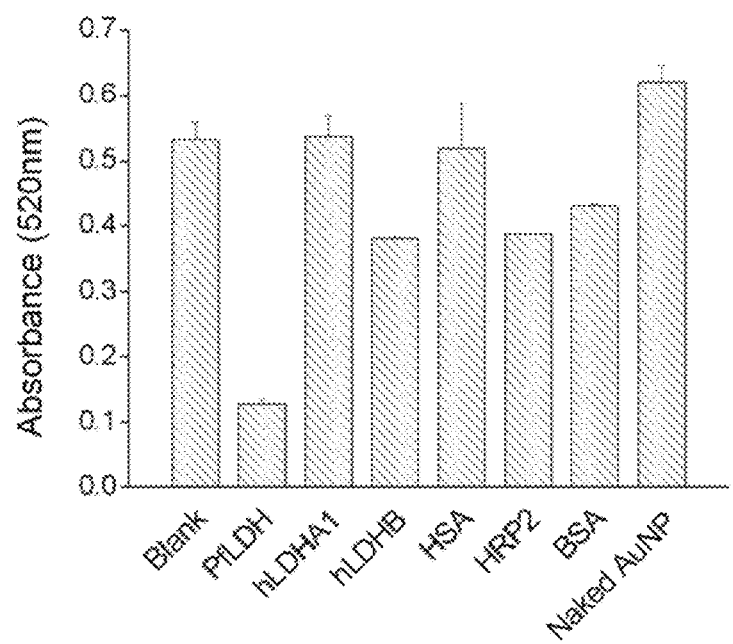

The PfLDH aptamer was conjugated to gold nanoparticles (AuNPs) to develop a colorimetric assay for PfLDH (FIG. 11a). Transmission electron microscopy revealed that the AuNP aggregated specifically in the presence of PfLDH (FIG. 11b). The characteristic ruby red color (absorbance peak of 520 nm) was specifically lost in the presence of 25 ng/μl PfLDH but not in the presence of hLDHA1, hLDHB or other controls (FIGS. 11c and 11d). The limit of detection was determined to be 0.73 ng/μl PfLDH.

The results show that the DNA aptamer identified can specifically recognize PfLDH due to its unique loop that is not present in human LDH. The results also show that the DNA aptamers of the invention can be used for diagnostic of malaria.

In conclusion, this Example shows the identification, structural characterization, and application of a specific embodiment of a hairpin DNA aptamer against PfLDH. This Example shows that the specificity of the DNA aptamer is achieved by discriminatory binding to a loop that is present only in the *Plasmodium*, but not present in the human lactate dehydrogenase, proving at the molecular level the utility of counter-selection in aptamer selection. The results show that the DNA aptamers of the present invention can be used for malaria diagnosis.

MATERIALS AND METHODS

Cloning, Expression and Purification of PfLDH and Human Lactate Dehydrogenases (hLDHA1 & hLDHB)

Open reading frame (ORF) of PfLDH was amplified by PfLDH-S(ATTATTGCTAGCATGGCACCAAAAG-CAAAAATCGTTTTAGTTG) (SEQ ID NO:12), and PfLDH-AS (ATTATTCTCGAGTTAAGCTAATGCCT-TCATTCTCTTAGTTTCA) (SEQ ID NO: 13), followed by ligation into the NcoI/XhoI digested pET-28a (Novagen) vector.

ORF of hLDHA1 was amplified by hLDHA1-S (ATTAT-TGAATTCATGGCAACTCTAAAGGATCAGCTGA) (SEQ ID NO:17), and hLDHA1-AS (ATTATTAAGCTTT-TAAAATTGCAGCTCCTTTTGGATC) (SEQ ID NO:18), followed by ligation into the NheI/HindIII digested pET-28a (Novagen) vector.

ORF of hLDHB was amplified by hLDHB-S (ATTAT-TGCTAGCATGGCAACTCTTAAGGAAAAACTCATT GCACC) (SEQ ID NO:19) and hLDHB-AS (ATTATTGCG-GCCGCTCACAGGTCTTTTAGGTCCTTCTGG) (SEQ ID NO:20), followed by ligation into the NheI/NotI digested pET-28a (Novagen) vector.

The plasmids were transformed into E. coli BL21 (DE3) pLysS for IPTG induced expression. The expressed proteins were further purified by using HisTrap column (GE Lifesciences).

In Vitro Selection of DNA Aptamers

A single-stranded DNA (ssDNA) library containing a 35-mer random region flanked by two 18-mer priming regions (5-CGTACGGTCGACGCTAGC-[N35]-CACGTG-GAGCTCGGATCC-3' (SEQ ID NO:14)) was used as starting material for in vitro selection. 2 nmol of ssDNA library was incubated with 1 nmol of target protein that was conjugated with Ni-NTA magnetic beads. The unbound species were removed and the ssDNA-protein-magnetic beads complexes were suspended in 10 μL of water for PCR amplification of PfLDH bound species by using forward primer (5'-CGTACGGTCGACGCTAGC-3') (SEQ ID NO:15) and reverse primer with biotinylated 5' end (5'-biotin-GGATC-CGAGCTCCACGTG-3') (SEQ ID NO:16).

PCR conditions were denaturation at 95° C. for 15 seconds, annealing at 50° C. for 30 seconds and elongation at 72° C. for 15 seconds for 10 cycles. Enriched DNA aptamer pool was purified by streptavidin magnetic beads followed by alkynylation to remove the unbiotinylated complementary strand. The resultant ssDNA pool was used for the next round of selection. Counter-selections by using Ni-NTA magnetic agarose beads, hLDHA1 immobilized Ni-NTA magnetic agarose beads and hLDHB immobilized Ni-NTA magnetic agarose beads were incorporated in between the SELEX cycles.

Crystallization and Structure Solution

The complex between PfLDH and the DNA aptamer was formed by mixing protein and DNA in a 1:1 molar ratio for crystallization. Screening of crystallization conditions was performed using MOSQUITO® liquid handler (TTP Labtech) at 291 K using sitting-drop vapor diffusion method by mixing 100 nl protein:DNA complex with an equal volume of crystallization solution. Of the 576 conditions screened, several hits for protein:DNA complex were observed. The best crystals were obtained under condition 26 of the Hampton Research Natrix Screen (0.2 M KCl, 0.1 M magnesium acetate, 0.05 M sodium cacodylate pH 6.5, 10% w/v PEG 8000).

The crystal of PfLDH:aptamer complex was cryoprotected in a solution of 30% glycerol mixed with the reservoir solution. Data were collected at beamline 13B1, NSRRC, Taiwan. Data were indexed and integrated with HKL2000. The structure was solved by molecular replacement using the program PHASER with the structure of LDH (PDB accession number 1LDG). The structure of the DNA aptamer was built manually with COOT and the complex structure was refined in Refmac.

Isothermal Titration Calorimeter (ITC)

For isothermal titration calorimetry, PfLDH aptamers and PfLDH were dialyzed in 25 mM Tris-HCl, pH 7.5 containing 0.1 M NaCl and 20 mM imidazole. All the buffers, protein and aptamers were degassed for 10 minutes at 25° C. prior to ITC experiments. All the experiments were performed in 25 mM Tris-HCl, pH 7.5 containing 0.1 M NaCl and 20 mM imidazole at 25° C. using iTC200 microcalorimeter (MicroCal Inc.). ITC experiment was carried out by injecting PfLDH aptamer into PfLDH. The ITC data were analyzed by using Origin v7.0 software (MicroCal Inc.) to integrate the titration curves for extracting the thermodynamic parameters, stoichiometry (N), equilibrium association constant [$K_a$ (=$K_d$−1)] and the binding enthalpy (ΔH).

Electrophoretic Mobility Shift Assay (EMSA)

Electrophoresis mobility shift assay was carried out by incubating 25 nM PfLDH aptamer 2008s with different proteins at concentrations ranging from 0-22.8 μM in 25 mM Tris-HCl, pH 7.5 containing 0.1 M NaCl and 20 mM imidazole in room temperature for 1 hour. Reactions were loaded on 12% native polyacrylamide gels and visualised by SYBR® gold nucleic acid gel stain (Invitrogen).

Surface Plasmon Resonance

Surface plasmon resonance (SPR) measurement was performed using a Biacore X100 instrument (GE Healthcare). PfLDH was captured on the surface of NTA sensor chip (GE Healthcare). A running buffer containing 25 mM Tris-HCl, pH7.5, 100 mM NaCl, 20 mM imidazole and 0.005% (v/v) TWEEN 20 was used for ligand capturing. The surface of the NTA chip was primed with running buffer and PfLDH aptamer, 2008s, was injected in triplicate with concentrations ranging from 0.625-10 μM by single-cycle analysis.

All experiments were performed at a flow rate of 30 μL min$^{-1}$ and at 25° C. All data were referenced for surface without captured PfLDH and blank injections of buffer. Sensorgrams were analyzed with Biacore X100 Plus Package evaluation software (GE Lifesciences).

Preparation of Aptamer-Immobilized Gold Nanoparticles

The PfLDH aptamer, 2008s, was conjugated to 10 nm gold colloid (Sigma) according to the protocol described by Taton[6] with modifications. All the incubations were carried out at room temperature in the dark. Disulfide-functionalized aptamer was reduced by 0.1 M dithiothreitol (DTT) for 30 minutes at room temperature prior to use. The reduced aptamers were purified using Sephadex G-25 (Pharmacia Biotech.). 2.5 nmol of reduced aptamers were then added to 500 μL of AuNP.

After 24 hours of incubation, 1 M NaCl and 0.1 M sodium phosphate buffer were added to reach final concentrations of 0.1 M NaCl and 10 mM phosphate buffer respectively. The aptamer/gold nanoparticle mixture was aged at room temperature for another 24 hours. 2008s-AuNP was separated from the solution by centrifugation followed by washing in 0.1 M NaCl/10 mM sodium phosphate buffer, pH 7. A 37-mer poly thymine (polyT) was conjugated to AuNP by the above procedures as the control experiment. The aptamer-AuNP conjugates were stored in 0.3 M NaCl/0.01% sodium azide/ 10 mM sodium phosphate buffer, pH 7.0.

Characterization of 2008s-AuNP: UV-Vis Spectrometry

The spectrometry analyses were carried out by Varioskan Flash Multimode Reader (Thermo Scientific). The spectrum was derived from at least three experiments.

Characterization of 2008s-AuNP: Transmission Electron Microscopy (TEM)

Oligonucleotides immobilised AuNPs were characterised by Philips CM100 TEM. Approximately 10 μL of AuNP conjugates were coated on a 200 mesh copper grid by adding sample to the grid and dried at room temperature.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

What is claimed is:

1. An aptamer for binding to *Plasmodium* lactate dehydrogenase, the aptamer comprising a nucleic acid sequence of SEQ ID NO: 2.

2. An aptamer according to claim 1, having 15-50 nucleotide bases.

3. An aptamer according to claim 1, wherein the aptamer is conjugated with one or more moieties selected from deoxythymidine nucleotide, inverted thymidine, and polyethylene glycol.

4. An aptamer according to claim 1, wherein the aptamer is an oligonucleotide having a backbone formed of deoxyribose-phosphate linkages.

5. An aptamer according to claim 1, wherein the aptamer is an oligonucleotide whose backbone comprises one or more deoxyribose-phosphate linkages stabilized by one or more thioester linkages and/or one or more amide linkages.

6. A kit comprising an aptamer according to claim 1, and a carrier.

7. A method for diagnosing *Plasmodium* infection in a subject, comprising:
   obtaining a biological sample from a subject;
   contacting the biological sample with a nucleic acid aptamer comprising a sequence of SEQ ID NO: 2;
   determining the formation of the binding complex between the nucleic acid aptamer and *Plasmodium* lactate dehydrogenase (LDH),
   wherein the presence of the binding complex indicates that the subject has *Plasmodium* infection.

8. The method, according to claim 7, wherein the presence of the binding complex indicates that the subject has *Plasmodium falciparum* infection.

9. The method, according to claim 7, wherein the biological sample is a blood or urine sample.

10. A method for detecting the presence of *Plasmodium* in a sample, comprising:
    contacting a sample with a nucleic acid aptamer comprising a sequence of SEQ ID NO: 2;
    determining the formation of the binding complex between the nucleic acid aptamer and *Plasmodium* lactate dehydrogenase (LDH), wherein the formation of the binding complex indicates the presence of *Plasmodium* in the sample.

11. The method, according to claim 10, further comprising determining the concentration or amount of the binding complex formed between the nucleic acid aptamer and *Plasmodium* lactate dehydrogenase (LDH).

12. The method, according to claim 10, wherein the presence of the binding complex indicates that the subject has *Plasmodium falciparum* infection.

* * * * *

UNITED STATES PATENT AND TRADEMARK OFFICE
CERTIFICATE OF CORRECTION

PATENT NO. : 9,000,137 B2
APPLICATION NO. : 13/763051
DATED : April 7, 2015
INVENTOR(S) : Julian A. Tanner et al.

Page 1 of 1

It is certified that error appears in the above-identified patent and that said Letters Patent is hereby corrected as shown below:

IN THE SPECIFICATION

Column 9,
Line 44, "and % or thio" should read --and/or thio--.

Column 10,
Line 44, "Plasmodium chaboudi" should read --Plasmodium chabaudi--.

Column 16,
Line 9, "IT2F" should read --1T2F--.
Line 15, "counter selection" should read --counterselection--.

Signed and Sealed this
Third Day of November, 2015

Michelle K. Lee
*Director of the United States Patent and Trademark Office*